Figure 1:
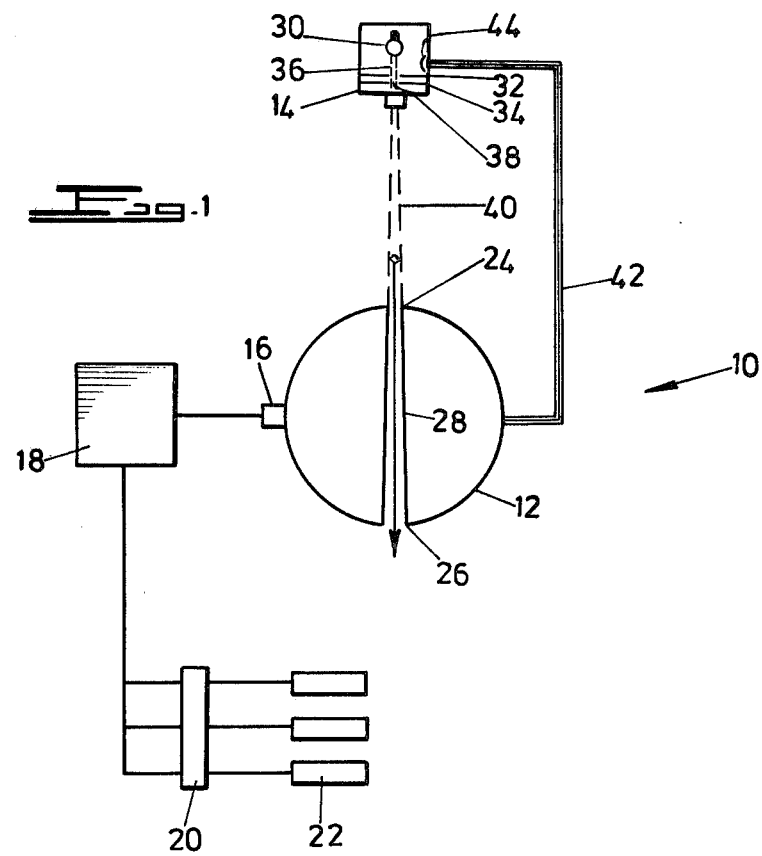

United States Patent [19]

Levitt et al.

[11] 4,186,838

[45] Feb. 5, 1980

[54] MEASUREMENT OF OPTICAL PROPERTIES

[76] Inventors: Charlie M. Levitt, 40 Craighall Rd., Victory Park, Johannesburg; Samuel Chatterley, 1 Reithaan St., Florida Lake, Florida, Johannesburg, both of South Africa

[21] Appl. No.: 825,390

[22] Filed: Aug. 17, 1977

[30] Foreign Application Priority Data

Aug. 27, 1976 [ZA] South Africa ............... 76/5149

[51] Int. Cl.² ............... B07C 5/342; G01N 21/26; G01J 3/38
[52] U.S. Cl. ............................ 209/581; 209/576; 250/228; 356/435; 209/914
[58] Field of Search ......... 209/111.5, 111.6, 111.7 R, 209/111.7 T, 73, 552, 556, 576, 577, 580, 581, 587, 588, 908, 914, 905, 922; 250/228, 226; 356/73, 256, 173, 201, 204–206, 402, 425, 432–435; 198/757

[56] References Cited

U.S. PATENT DOCUMENTS

| | | | |
|---|---|---|---|
| 2,263,938 | 11/1941 | West | 250/226 X |
| 2,646,880 | 7/1953 | Frankel | 209/111.6 |
| 2,678,725 | 5/1954 | Jacobson | 209/111.6 |
| 2,759,601 | 8/1956 | Baigent | 209/111.6 |
| 3,058,588 | 10/1962 | Palmquist | 209/111.7 R X |
| 3,150,264 | 9/1964 | Ehlert | 250/228 UX |
| 3,171,538 | 3/1965 | Hagenbook | 198/757 X |
| 3,197,647 | 7/1965 | Fraenkel | 209/111.7 T X |
| 3,260,347 | 7/1966 | Barnes | 198/380 |
| 3,283,896 | 11/1966 | Jirik et al. | 209/908 X |
| 3,489,277 | 1/1970 | Silverman | 209/908 X |
| 3,490,849 | 1/1970 | Hambleton | 356/206 X |
| 3,838,926 | 10/1974 | Kato et al. | 250/228 X |
| 3,914,601 | 10/1975 | Hoover et al. | 209/587 X |

*Primary Examiner*—Joseph J. Rolla
*Assistant Examiner*—Edward M. Wacyra
*Attorney, Agent, or Firm*—Cushman, Darby & Cushman

[57] ABSTRACT

The colors or surface conditions of small articles are determined by passing the articles through an integrating sphere and separately illuminating the articles before they enter the sphere, during their passage through the sphere and after they leave the sphere. The light transmitted through or reflected by each article is collected by the sphere and passed to analyzing apparatus. The articles are sorted according to the measurements.

11 Claims, 3 Drawing Figures

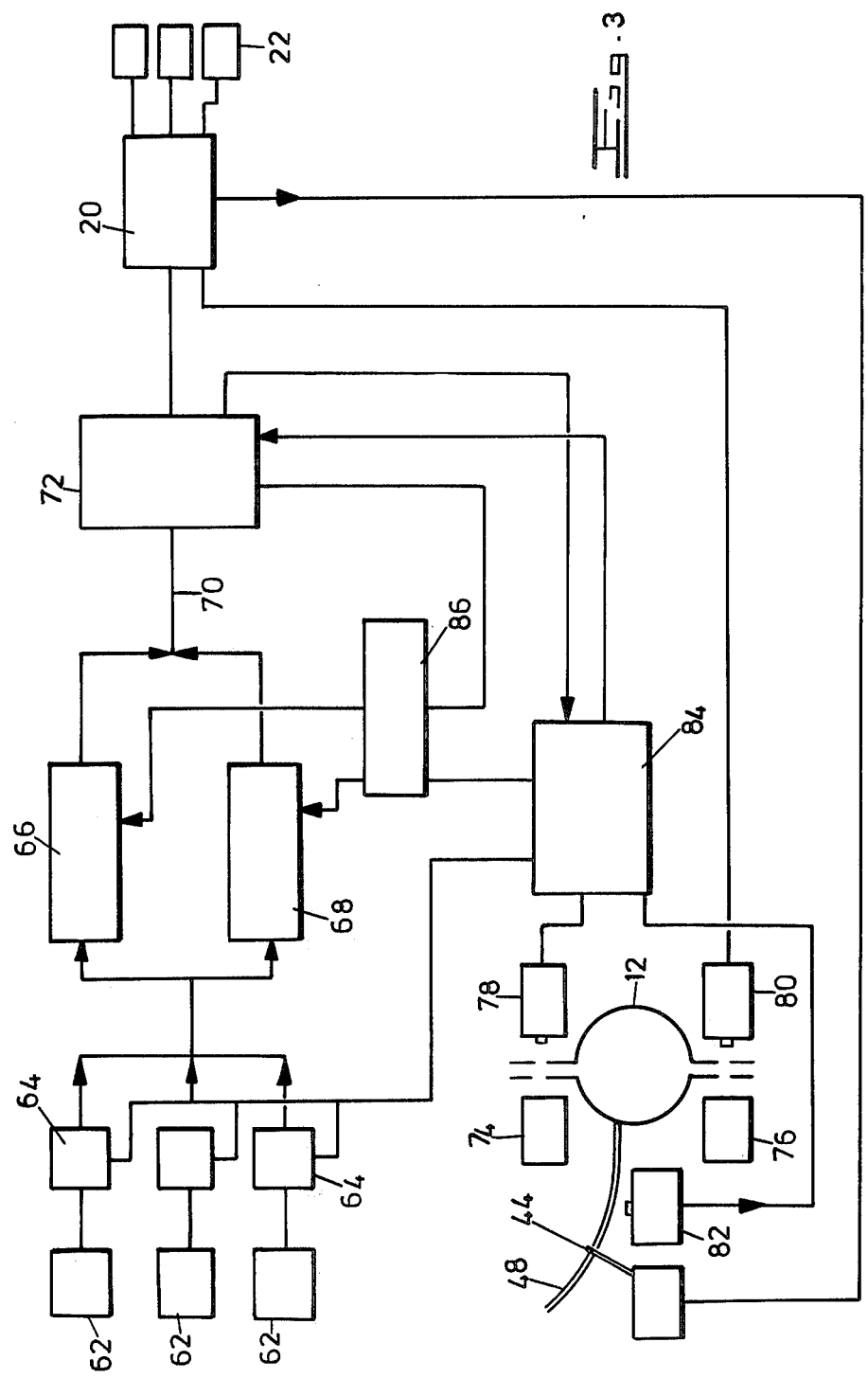

MEASUREMENT OF OPTICAL PROPERTIES

This invention relates to the measurement of the colour of small articles. The invention is particularly suited for the measurement of the colour of polished and unpolished gems and near gems, and industrial and synthetic diamonds.

In one way of measuring the colour of a diamond, the diamond is illuminated and viewed against one or more backgrounds of known colour. T is method suffers from the disadvantages that the colour determination is dependent on the orientation of the diamond during its illumination, and it does not easily lend itself to the precise sorting of large quantities of diamonds.

It is an object of the present invention to provide an improved method of measuring the colour of small articles.

The invention provides a method of measuring the colour of a small article which includes the steps of passing the article through an integrating sphere, illuminating the article during at least part of its passage with a beam of radiation of a suitable wavelength, and detecting the radiation transmitted or reflected by the article onto the internal wall of the sphere.

While the article may be passed transversely through the beam it is preferred that the article is passed through the sphere along the path of the beam so that the article is illuminated during its entire passage through the sphere. This step permits the radiation to be incident on the article for a maximum period. Different surfaces of the article are consequently illuminated and the detected radiation can be averaged to arrive at an average value of the colour of the article. If desired a spinning movement could be imparted to the article to ensure that all surfaces of the article are exposed to the incident beam of radiation. Spurious readings due to the orientation of the article are thereby largely eliminated.

The article may be illuminated by the beam as it enters or before it enters the sphere. In this case it is only the radiation which is transmitted by the article onto the internal wall of the sphere which is detected. The detected signal, although subject to the orientation of the article, is therefore a measure of the transparency of the article.

Similarly if the article is illuminated by the beam as it leaves or after it has left the sphere, it is only the radiation which is reflected by the article onto the internal wall of the sphere which is detected. The detected signal which is also dependent on the orientation of the article is a measure of the reflectivity of the article.

The invention also provides apparatus for measuring the colour of a small article which comprises an integrating sphere, an inlet and an outlet in the wall of the sphere to permit the passage of the article through the sphere, means to project a beam of radiation of a suitable wavelength through the sphere so that the article is illuminated during at least part of its passage, and means to detect the radiation transmitted or reflected by the article onto the internal wall of the sphere.

In a preferred form of the invention the direction of the beam of radiation through the sphere is coincident with the direction of travel of the article through the sphere.

Further according to the invention the apparatus includes means responsive to the detecting means to sort the article leaving the sphere according to its colour.

Further according to the invention the apparatus includes means to introduce a succession of the articles into the sphere, the introducing means comprising a tray, a ramp spiralling upwardly from the centre of the tray towards the periphery of the tray, means circularly to oscillate the tray so that articles deposited at the centre of the tray move up the ramp, the articles becoming regularly spaced from each other by this movement, a circular array of nozzles which is rotated past the upper end of the ramp in synchronism with the articles moving up the ramp, and means to apply a vacuum to each of the nozzles to cause it to pick up an article from the ramp and to release the vacuum when the article is positioned above the inlet of the sphere.

Figure 2:
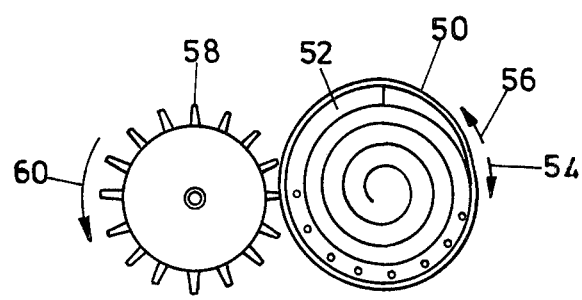

The invention is further described by way of example with reference to the accompanying drawings in which:

FIG. 1 is a diagrammatic side view of colour measuring apparatus according to the invention, FIG. 2 is a diagrammatic plan view of the apparatus used to introduce articles into the apparatus of FIG. 1, and FIG. 3 is a diagram of an electrical circuit used with the apparatus of the invention.

Referring to FIG. 1 colour measuring apparatus 10 consists of an integrating sphere 12 which is coated internally with a barium sulphate photometric paint of neutral spectral reflectance, a light source 14, a detector 16, analyzing and computing circuitry 18 which controls blast drive apparatus 20, and a linear array of blast nozzles 22 connected to the apparatus and arranged below the sphere 12.

The sphere 12 has an inlet 24 and an outlet 26. A quartz tube 28 extends between the inlet and the outlet. The tube tapers slightly outwardly towards the outlet 26.

The light source 14 includes a quartz iodine globe 30. The tube 28 is substantially transparent to the light produced by this globe. Two plates 32 and 34 with collimated holes 36 and 38 respectively are positioned to produce a beam of substantially collimated light 40. Nonetheless the beam does diverge and the arrangement is such that the cross-section of the tube 28 is slightly larger than the cross-section of the beam 40 to ensure that the beam does not impinge on the wall of the tube. A fibre optic coupling 42 leads from the light source 14 to the interior of the sphere, the transmission of light through the coupling being controlled by means of a shutter 44.

The detector 16 includes three filters which each pass different dominant wavelengths, and three photomultiplier tubes to measure the intensity of the light passed by each filter. The outputs of the three tubes are connected to a comparator, and the comparator output signal controls the operation of the blast drive apparatus 20.

FIG. 2 illustrates in plan apparatus which is used to introduce articles into the sphere 12 of FIG. 1. This apparatus consists of a circular tray 50 which has a ramp 52 spiralling upwardly from the centre of the tray towards the periphery of the tray. A motor (not shown) beneath the tray rotates the tray slowly, via a clutch, in the direction of the arrow 54 i.e. in the upward direction of the ramp. The clutch is designed intermittently to disengage the motor drive from the tray whereupon the tray under the action of a spring rotates rapidly but for a short time only in the direction of the arrow 56. The result of this arrangement is that the tray is circularly oscillated slowly in one direction and rapidly in the reverse direction and articles deposited at the centre of the tray move slowly up the ramp and become regularly spaced from one another.

A circular array of nozzles 58 is rotated alongside the tray 50 in the direction of the arrow 60. By regulating the oscillatory movement of the tray and the rotational speed of the nozzles, the nozzles can be synchronized with the articles as they move up the ramp, near the upper end of the ramp, and each nozzle as it nears the ramp is aligned with a single article on the ramp.

A vacuum source (not shown) is applied to the various nozzles 58 as they approach the ramp and causes the individual articles to be picked up by the nozzles. The apparatus shown in FIG. 1 is positioned above and to one side of the sphere 12 so that the path of travel of the nozzles 58 remote from the tray 50 extends over the inlet 24 of the sphere. Each nozzle is connected to the vacuum source through a small solenoid valve. A sensor (not shown) detects the presence of each nozzle above the inlet 24 and causes its valve to be closed so that the vacuum applied to the nozzle is released. As the nozzle moves away from the inlet 24 the valve opens and the vacuum is again applied to the nozzle.

In use the articles, for example diamonds, the colours of which are to be measured, are placed in the centre of the tray 50 and the apparatus is operated as described above. This causes the diamonds to be picked up individually by the nozzles 58. As these nozzles pass above the inlet 24 the vacuum is released and the diamonds thus fall one at a time, and at a controlled rate, through the sphere 12. The diamonds as they fall are guided by the tube 28, and therefore are constantly illuminated during their passage through the sphere. When there are no diamonds in the light beam 40, the beam passes directly through the sphere and no light is scattered onto the internal wall of the sphere. The photomultiplier tubes in the detector 16 therefore exhibit zero response.

As a diamond enters the sphere at the inlet 24 part of the light transmitted through the diamond is directed onto the internal wall of the sphere. This light is gathered by the sphere and passed through the filters to the photomultiplier tubes. The intensities of the signals produced by the tubes as the diamond enters the sphere are a measure of the transparency of the diamond, for none of the light reflected by the diamond is detected by the photomultiplier tubes.

Conversely, as the diamond leaves the sphere the signals produced by the photomultiplier tubes are a measure of the reflectivity of the diamond for the light which is transmitted by the diamond cannot reach the detector 16.

During its passage through the sphere the diamond is constantly illuminated. Since the diamond falls freely its orientation changes continuously and it is illuminated from all sides. The light reflected and transmitted by the diamond onto the internal wall of the sphere is detected by the photomultiplier tubes and the signals produced by them can be averaged to arrive at an average determination of the colour of the diamond, independent of the orientation of the diamond.

At least two of the signals produced by the photomultiplier tubes are compared in intensity to categorize the diamond into a predetermined colour group. If desired more than three filters, and three photomultiplier tubes, could be used to analyse the colour of the diamonds with more precision. The trajectories of the diamonds as they leave the sphere extend past the blast nozzles 22, and depending on the computed colour of the diamond the appropriate nozzle is actuated at the correct instant to blast the diamond into the collecting bin.

The apparatus of the invention is able automatically to sort large quantities of diamonds at a high rate, and simultaneously to overcome orientation effects. In addition the transparency and the reflectance of each diamond can be individually measured and the diamond may then be sorted. In other words, diamonds may be sorted according to their surface condition of the reflectance and transparency measurements will depend on those surface conditions which affect the amount of radiation which would otherwise have been reflected or transmitted by the diamond.

The principle of measuring the reflectance or transparency of an article by illuminating the article while it is outside the sphere, and collecting the reflected or transmitted radiation by means of the sphere, can be realized in other ways to that described. For example, the articles could be moved past the inlet or the outlet of the sphere, as the case may be, through a beam of radiation, and never pass through the sphere. While an arrangement of this nature would not normally overcome orientation effects it would generally be less complex and easier to implement.

Use is made of the fibre optic coupling 42 to normalize the apparatus. At regular intervals, preferably once per revolution of the array of nozzles 58, the feed of the diamonds is interrupted and the shutter 44 is moved so that light from the source 14 is introduced into the sphere by means of the coupling. The signals produced by the detector 16 depend on the spectrum of light produced by the globe 30, the reflecting properties of the paint inside the sphere, the detection characteristics of the photomultiplier tube, and on the electronic circuitry used to process the signals from the photomultiplier tubes.

The detector output signals are compared to reference signals which are set up initially by passing a standard set of diamonds of known colour through the sphere. Apart from this the intensity of the globe 30 is constantly monitored by a light sensitive device which automatically varies the voltage applied to the globe to maintain the light intensity within present limits. These operations ensure that a high accuracy and consistency is achieved in the colour determination of the diamonds.

FIG. 3 illustrates in block diagram form the electronic circuit used to compute the colours of the diamonds and to control the ejectors, or blast nozzles 22.

The apparatus consists of three photomultiplier tubes 62 which are connected by means of analogue to digital converters 64 to memories 66 and 68. A data bus 70 connects the memories to a microprocessor 72 which controls the blast drive apparatus 20.

Light emitting diodes 74 and 76, together with phototransistors 78 and 80, at the inlet and outlet respectively of the integrating sphere 12, are used to detect the entrance to and the exit from the sphere of each diamond.

Light conducted through the fibre optic coupling 48 is detected by means of a phototransistor 82 which is connected to an address clock timing and logic unit 84.

An address line change over switch 86 is used to channel data from the analogue to digital converters 64 to the memories 66 and 68.

The circuitry functions as follows: before a diamond enters the sphere 12 the beam of light from the light emitting diode 74 is interrupted. This produces a pulse which initiates the hardware address clock and timing logic circuitry 84. If desired a delay which is set in the program of the microprocessor 72 may be initiated to allow the diamond to enter the sphere before the measurement cycle starts. The period between measurements is also set by a software instruction.

During each measurement cycle, the voltage signals from the three photomultiplier tubes 62 are simultaneously converted to their binary equivalents by the analogue to digital converters 64. The binary values are written sequentially into one of the memories, say memory 66, under the control of the address clock timing and logic unit 84. This procedure is repeated until the memory is full whereupon the memory address and read write switch 86 is switched and the memory 66 is connected to the microprocessor bus 70. At the same time the memory 68 is placed under the control of the logic unit 84 to accept data from the next diamond which falls through the sphere 12.

When the memories are switched, an interrupt is given to the microprocessor which now leaves the service routine and commences processing the data in memory 66. When a decision is made regarding the colour of diamond the microprocessor sends a signal to the correct ejector drive circuit. This circuit is only activated when the diamond interrupts the light beam emitted by the light emitting diode 76 at the bottom of the sphere and the particular ejector is fired after the correct time delay.

The circular array of nozzles 58 (see FIG. 2) carries a dummy metal nozzle in place of one of the vacuum nozzles. Once per revolution, a proximity switch is activated by the dummy metal nozzle and the shutter 44 is opened allowing light through the light guide 48 into the sphere 12. This light is detected by the photo transistor 82, which in turn activates the logic unit 84. Readings are taken as before, but a special program in the microprocessor 72 analyses the colour balance of the light, and compares this to standard values, and if this is out of specification, the apparatus stops operating.

As the unit is microprocessor based, it has the ability to make complex logic decisions under program control. Microprocessor control further enhances versatility as many different sort program may be used.

We claim:

1. Apparatus for measuring the colour of an article which comprises an integrating sphere, first and second opposed apertures being formed in the wall of the sphere to permit the passage of the article through the sphere, means to project a beam of radiation of a suitable wavelength from outside the sphere through the first aperture and the interior of the sphere to the second aperture so that the article is illuminated during at least part of its passage, and means to detect the radiation diverted by the article onto the internal wall of the sphere.

2. Apparatus according to claim 1 in which the article is illuminated during its entire passage through the sphere.

3. Apparatus according to claim 1 which includes a tube which extends inside the sphere from the first aperture to the second aperture, the tube being made from a material which is substantially transparent to the radiation and having an internal cross-section which is slightly larger than the cross-section of the beam of radiation.

4. Apparatus according to claim 1 which includes means to introduce a succession of the articles into the sphere, the introducing means comprising a tray, a ramp spiralling upwardly from the centre of the tray towards the periphery of the tray, means to circularly oscillate the tray so that articles deposited at the centre of the tray move up the ramp, the articles becoming regularly spaced from each other by this movement, a circular array of nozzles which is rotatable past the upper end of the ramp is synchronism with the articles moving up the ramp, and means to apply a vacuum to each of the nozzles to cause it to pick up an article from the ramp and to release the vacuum when the article is positioned above the inlet of the sphere.

5. A method of measuring the colour of an article which includes the steps of passing the article through an integrating sphere along the path of a beam of radiation of a suitable wavelength which emanates from outside the sphere and traverses the interior of the sphere, the article being thereby illuminated by the radiation during at least part of its passage through the sphere, and detecting the radiation diverted by the article onto the internal wall of the sphere.

6. A method according to claim 5 in which the article is illuminated during its entire passage through the sphere.

7. A method according to claim 5 in which the article passes through the sphere in the direction of radiation of the beam and only that radiation which is transmitted by the article as it enters the sphere is detected.

8. A method according to claim 5 in which the article passes through the sphere in the direction of radiation of the beam and only that radiation which is reflected by the article as it leaves the sphere is detected.

9. A method according to claim 5 including the step of constraining the movement of the article by means of a suitable guide inside the sphere to ensure that the article is illuminated during its entire passage through the sphere.

10. A method of sorting articles according to the reflectance of the articles which includes the steps of passing the articles in succession through an integrating sphere, illuminating each article with a beam of radiation of a suitable wavelength directed along the path of the article after the article has passed through the sphere, detecting the radiation reflected by the article onto the internal wall of the sphere, and sorting the article according to the detected radiation.

11. A method of sorting articles according to the transparency of the articles which includes the steps of passing the articles in succession through an integrating sphere, illuminating each article with a beam of radiation directed along the path of the article before it enters the sphere, detecting the radiation transmitted through the article onto the internal wall of the sphere, and sorting the article according to the detected radiation.

* * * * *